US00H002271H

(19) United States
(12) Statutory Invention Registration
Sears

(10) Reg. No.: US H2271 H
(43) Published: Jul. 3, 2012

(54) PRODUCTION AND APPLICATION OF AN AIRCRAFT SPREADABLE, CYANOBACTERIAL BASED BIOLOGICAL SOIL CRUST INOCULANT FOR SOIL FERTILIZATION, SOIL STABLIZATION AND ATMOSPHERIC CO2 DRAWDOWN AND SEQUESTRATION

(76) Inventor: James Thomas Sears, Boulder, CO (US)

(21) Appl. No.: 13/373,352
(22) Filed: Nov. 12, 2011

Related U.S. Application Data

(60) Provisional application No. 61/422,613, filed on Dec. 13, 2010.

(51) Int. Cl.

| | |
|---|---|
| ***C05F 11/08*** | (2006.01) |
| ***A01G 7/00*** | (2006.01) |
| ***C12N 1/12*** | (2006.01) |

(52) U.S. Cl. ..... 71/6; 47/1.4; 47/48.5; 435/170; 435/177; 435/289.1; 504/117

(58) Field of Classification Search ..... 71/6, 71/7, 8; 47/1.4, 48.5; 435/170, 176, 177, 435/289.1; 504/117
See application file for complete search history.

(56) References Cited

U.S. PATENT DOCUMENTS

| | | | |
|---|---|---|---|
| 3,969,844 | A | 7/1976 | Fogel |
| 4,774,186 | A | 9/1988 | Schaefer |
| 4,879,232 | A | 11/1989 | MacDonald |
| 4,921,803 | A | 5/1990 | Nohr |

(Continued)

OTHER PUBLICATIONS

Klaus S. Lackner, A Guide to CO2 Sequestration, Science Jun. 13, 2003: vol. 300 No. 5626 pp. 1677–1678 DOI: 10.1126/science.1079033.

Mike Maki, Algae—A New Source of Soil Fertility, Tilth, V. 8, No. 1 & 2, 1982 (Soil Supplement), Tilth Producers Quarterly.

Matthew Bowker, Biological Soil Crust Rehabilitation in Theory and Practice: An Underexploited Opportunity, Restoration Ecology (2007) vol. 15, Issue 1, pp. 13–23.

Richard Stone, Have Desert Researchers Discovered a Hidden Loop in the Carbon Cycle? Science Jun. 13, 2008: vol. 320, No. 5882, pp. 1409–1410 DOI: 10.1126/science.320.5882.1409.

*Primary Examiner*—Daniel Pihulic

(57) ABSTRACT

Systems and methods are described for the production and application of a cyanobacteria based biological soil crust inoculant for soil fertilization, soil stabilization and the drawing down and sequestering of atmospheric carbon. Inoculant is generated as a dry granulate that can be stockpiled and spread onto soils using standard agricultural spreading practices employing aircraft, ground equipment and irrigation systems. This inoculant will have particular application in stabilizing agricultural and arid land soils to limit their erosion, increasing soil fertility by fixing atmospheric nitrogen and providing nutrients, and drawing down atmospheric carbon dioxide by stimulating the growth and propagation of these biological soil crusts and their associated microorganisms and vascular plants. The effect of this carbon dioxide draw down will further the broad scale application of the soil crust inoculant by industries and nations interested in offsetting their anthropogenic carbon dioxide emissions while increasing the fertility of their soils.

19 Claims, 6 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

Belt extraction, compounding and drying

U.S. PATENT DOCUMENTS

| | | | | |
|---|---|---|---|---|
| 4,950,601 | A | 8/1990 | MacDonald | |
| 6,228,136 | B1 | 5/2001 | Riley | |
| 7,524,514 | B2 * | 4/2009 | Brekke | 424/488 |
| 8,011,132 | B2 | 9/2011 | Pearce | |
| 8,029,593 | B2 | 10/2011 | Amy | |
| 2003/0203491 | A1 * | 10/2003 | Andrevski et al. | 436/46 |
| 2008/0236227 | A1 | 10/2008 | Flynn | |
| 2009/0164014 | A1 * | 6/2009 | Liljensten et al. | 623/16.11 |
| 2010/0068721 | A1 * | 3/2010 | Gressel et al. | 435/6 |
| 2010/0116734 | A1 * | 5/2010 | Wiemers et al. | 210/619 |
| 2010/0224574 | A1 | 9/2010 | Youngs | |
| 2011/0143012 | A1 * | 6/2011 | Rettenmaier | 426/648 |

* cited by examiner

Field of the Invention

Production process

Closed Photobioreactor

Belt extraction, compounding and drying

Flake Granulation and Coating

CO2 Storage Buffer

PRODUCTION AND APPLICATION OF AN AIRCRAFT SPREADABLE, CYANOBACTERIAL BASED BIOLOGICAL SOIL CRUST INOCULANT FOR SOIL FERTILIZATION, SOIL STABLIZATION AND ATMOSPHERIC CO2 DRAWDOWN AND SEQUESTRATION

CROSS-REFERENCE TO RELATED APPLICATIONS

This application claims priority from U.S. Provisional patent application Ser. No. 61/422,613, filed Dec. 13, 2010, entitled "Production and Application of Cyanobacterial Based Photosynthetic Soil Fertilizer", the contents of which are incorporated herein by reference.

FIELD OF THE INVENTION

The present invention is related to production and application of cyanobacterial based photosynthetic soil fertilizer.

BACKGROUND OF THE INVENTION

Build-up of atmospheric carbon dioxide is expected to have a detrimental impact on global weather conditions. Accordingly, there is a need for additional systems and/or methods that assist in mitigating the build-up of atmospheric carbon dioxide, including the sequestering of industrial CO2 emissions. Additionally, there is a need for a natural soil fertilizer that mitigates desertification and revitalizes the soil micronutrients depleted by chemical farming.

Soil microorganisms within BSC form a symbiotic group; a mutually beneficial relationship exists among components within the group, and with the plants in the associated healthy soil. Many of the microorganisms in BSC are photosynthetic and draw their energy from sunlight such that they can, in turn, manufacture and provide nutrition and fixed nitrogen to cohort microorganisms that are not photosynthetic or are found deeper in the soil. The actions of the BSC, and the deeper cohort microorganisms it supplies nutrition to, work together as a symbiotic group to stabilize soil and draw plant available nutrition from the grains of soil into the soil matrix over time. In addition, the dominant cyanobacteria component of BSC fixes carbon as well as nitrogen from the atmosphere. Beginning with BSC, the combined actions of these microorganisms create conditions benefiting the establishment and growth of vascular plants like grasses, shrubs and crops. In effect, the BSC is a naturally occurring solar powered fertilizer that lives on the surface of bare earth making it suitable and beneficial for the establishment of vascular plants over time.

However, because BSC microorganisms reproduce slowly in dry climates and are not very motile, physical disturbances like tilling, livestock grazing, and fire can halt the BSCs beneficial effects for the soil and the BSC, and these benefits can take decades or centuries in dry climates to naturally restore. Of the planet's 13 billion hectares of land mass, about 1 billion hectares of BSC supported soil have been damaged by human activity that has led to increased global desertification and airborne dust that exacerbates the effects of global warming. Once BSC activity declines, the vascular plants dependent on healthy soil decline, further reducing the ability of the land to produce crops, prevent erosion, and draw down CO2 from the atmosphere. Additionally, the use of factory fertilizers based on the energy-intensive Haber-Bosch process for fixing agricultural nitrogen increase levels of atmospheric CO2, pollute waterways with excess nitrogen run off, and deplete soil health and micronutrients.

The following prior art illustrates the progress made so far in the culturing and dissemination of cyanobacterial algae for the purpose of inoculating dry or damaged land with a living fertilizer in order to rejuvenate the biological soil crust, enable the growth of vascular plants, and sequester atmopheric CO2.

The use of cyanobacterial (blue-green) algae as a fertilizer has been proposed by U.S. Pat. Nos. 4,879,232 and 4,950,601, both to MacDonald et al., and by U.S. Pat. No. 4,921,803 to Nohr.

In U.S. Patent Application Publication No. 2008/0236227 to Flynn (herein after referred to as "Flynn"), a biological culture of natural soil microorganisms is drawn from their normal residence in the top centimeter of healthy undisturbed soil found in un-shaded areas. These blue-green algae and their soil consortia can be cultured into an inoculant in a manner taught by Flynn and used to inoculate a photobioreactor (or PBR) where the culture is grown in liquid media with ready access to nutrients, carbon dioxide, and light. Once the culture has increased in mass sufficiently, the inoculant is harvested and dehydrated for storage and later dissemination across arid land. Additives may be added such as fungi, other bacteria, mineral salts, and xeri-protectants. Flynn reports that certain methods of particle reduction, such as grinding, can cause cell damage that results in a lower rate of recovery for the dried inoculant, once exposed to sun and water. Pelletizing the inoculant via extrusion enhances survivability, but may not be the ideal aerodynamic size and shape for wide- spread dissemination, such as by aircraft crop dusting.

U.S. Pat. No. 4,774,186 to Schaefer Jr. et al. (herein after referred to as "Schaefer") discloses an aqueous suspension comprising water, algae, and a carrier which is applied to the soil using a conventional irrigation system. The carrier comprises water dispersible particles, such as clay, lactose and other additives. The carrier is mixed with algae that is in a resting stage (essentially dry, dormant, and revivable) to produce a dry, flowable mixture which is then added to water near the site of application. Because the carrier will eventually be dissolved in water prior to application, it may not have the homogeneity that a compounded mixture destined for dry dissemination would need.

Youngs, in U.S. Patent Application Publication No. 2010/0224574 (herein after referred to as "Youngs"), teaches a method of water extraction from a culture of algae or other mixture. Herein, a culture of inoculant from a PBR is fed into a filter system that uses a capillary belt to efficiently remove the water from a desired soil inoculant, leaving a thin mat of moist algae that is substantially dry. Further dryers or air drying is employed to reduce the moist mat of algae to a dried and live flake that can be stored for later dissemination upon in arid land. Youngs, which is incorporated herein by reference, enables a large scale drying of algae and soil microorganisms to produce a viable algae particle.

The use of conventional PBR methods of culturing soil microorganisms in closed tanks results in a slow growth rate due to, among other reasons, sunlight penetrating the growth media by only centimeters, this growth rate being insufficient for large scale is production. U.S. Pat. No. 6,228,136 B1 issued to Riley et al (herein after referred to as "Riley") teaches a method of growing thin-film cyanobacterial soil inoculant on a substrate made of hemp/cotton cloth and other materials. In Riley, the substrate provides for a faster growth rate since sunlight can easily penetrate a thin layer of growth media. The harvested substrate/algae is then dried and either laid onto the soil or chopped up and disseminated. Low temperature drying preserves the viability of the dried inoculant. Spools of substrate/algae can be wound up for more compact storage. The substrate pieces or sheets represent additional bulk and need to eventually disintegrate into the soil.

Underground injection of CO2 as a method of sequestering CO2 is proposed by Lackner in "*A Guide To CO2 Sequestration*", SCIENCE Magazine, Vol. 300 Jun. 13, 2003. This CO2 is best provided by concentrated sources, such as industrial plants emitting CO2.

CO2 uptake by a growing culture of inoculant will vary by around a factor of 2 or more through a 24 hour cycle as the sunlight varies. The availability of higher concentrations of CO2 than are available from the atmosphere may enhance the growth rates of a culture, were they available. Also, emissions from an industrial source of CO2, such as a coal burning power plant, vary substantially across a day or days. There is currently no known coupling of an industrial source to a PBR culturing system that accounts for variations in industrial output.

Several shortcomings exist within the existing art that prevent large scale production, storage, and dissemination of a BSC inoculant. Rot and short shelf life of dried inoculant are key impediments; it is crucial that the inoculant is gently and thoroughly dried and preserved. Different soil types and dissemination methods require a different consortia of soil microorganisms having incompatible growth conditions, different optimum preservatives and nutrients, and different particle shape and size. For instance, aircraft crop dusting would likely require a different inoculant composition than land-based spreading or delivery through an irrigation system. What's needed is a flexible culturing and compounding system that can adapt the manufacturing process to maximally grow and preserve a symbiotic consortium of inoculant particles for a wide variety of target soil and dissemination methods on a large scale. Excess bulk, such as that created by a substrate method, should be avoided to eliminate the problem of decomposing substrate material and the additional bulk that would burden production, storage, and dissemination processes. There is therefore a need for a high capacity substrateless system of production. Also, the financial and technical challenges of any new technology requires leveraging any and all available synergies and options.

SUMMARY OF THE INVENTION

It is to be understood that the present invention includes a variety of different versions or embodiments, and this Summary is not meant to be limiting or all-inclusive.

In the general invention, a biological culture of natural soil microorganisms is drawn from the top centimeter or so of healthy undisturbed soil found in un-shaded areas, as taught by Flynn. Blue-green algae and the soil consortia are cultured into an inoculant within one or more photobioreactors (PBRs), as part of a PBR system. CO2 is optionally coupled into the closed PBR system through a storage buffer located above ground or within subterranean pore space in order to leverage sequestering incentives and to cope with variable rates of CO2 industrial emissions and culture uptake. The combined soil microorganisms are harvested and compounded using an integrated water extraction and compounding system, described further below. Admixes (additives) and coatings are added to create a wide variety of deliverable soil microorganisms products that can be spread upon targeted farmlands or damaged land using standard agricultural practices, such as crop dusting, mixing with irrigation water or applying with spreading machines. Particle shaping processes create final forms and densities to suit the needs of the final product. As microorganisms grow and propagate in and on the soil, their uptake of CO2 from the atmosphere increases proportionate with the population size, impinging sunlight, water availability, soil type and the occurrence of secondary vascular plant growth that might further increase the net primary productivity of the soil.

The one or more embodiments of the invention described herein includes improved methods for the production, application and utilization of cyanobacterial based photosynthetic soil fertilizer, herein also called by its prospective trade name of "TerraDerm." An overview of these improvements and the role of TerraDerm are illustrated in FIG 1. As stated previously, soil microorganisms form a biological soil crust ("BSC") that serves many functions, including gluing the soil grains in place, thereby limiting wind and water erosion, as well as providing fertilization and plant vitality.

The benefits of developing TerraDerm for commercial agriculture fertilization and, in fact for a global reseeding program, are numerous, and include:

1) Repairing the 1 billion hectares of BSC supported soil that have been damaged by human activity, reducing the desertification and airborne dust that exacerbates the effects of global warming;
2) Offsetting or replacing the use of factory fertilizers that are based on the in energy intensive Haber-Bosch process for fixing agricultural nitrogen, which raises CO2 levels and pollutes nearby waterways.
3) Supporting sustainable and organic farming practices that focus on the natural health of the soil, which derives and makes bio-available plant micronutrients directly from the soil grains within.
4) Drawing increasing amounts of carbon from atmospheric CO2 into the soil where that carbon becomes part of a living sustainable microbiological community, effectively sequestering this atmospheric carbon into the soil.

This atmospheric carbon drawdown effect is expected to be highly significant as TerraDerm and the inventive production and application concepts described herein are commercially propagated. Through TerraDerm soil inoculation, its natural propagation on the soil, and secondary vascular plant growth enhancement, it has been estimated that the conversion of 1 ton of CO2 into TerraDerm then applied onto suitable soils can cause the drawdown of up to 50 tons of CO2 from the atmosphere annually through direct photosynthetic uptake of atmospheric gasses by that soil. Accordingly, the industrial community has interest in using TerraDerm production and applying this carbon multiplier drawdown effect to offset their atmospheric emissions of CO2.

FIG. 1 summarizes the entire process. First a biological culture of natural soil microorganisms is drawn from their normal residence in the top centimeter of healthy undisturbed soil found in un-shaded areas. These blue-green algae and their soil consortia are cultured into an inoculant in a manner taught by Flynn (U.S. Patent Application Publication No. 2008/0236227) and used to inoculate an amplifying photobioreactor, also taught by Flynn, where the culture can be rapidly grown in liquid media via ready access to nutrients, carbon dioxide, sunlight and using hydraulic mixing. The photobioreactor can be effected through a number of designs differing in levels of performance and features; however the preferred designs are biologically closed so that the soil crust microorganisms can be grown in an environment protected from invasion by competing algal species that may be better adapted for propagating in the aqueous environment. The PBR is fed by sunlight, nutrients and a carbon source that is most commonly carbon dioxide, but that may be a fixed form such as sodium bicarbonate or other bio-available forms. In highly scaled systems, if the carbon is from an industrial source in the form of CO2, then a CO2 storage buffer system can help match the industrial delivery rate with the biological uptake rate of CO2 by the PBR.

PBRs may be an arrangement of 2 or more parallel PBRs that separately cultivate 2 or more components of the final consortium of cyanobacterial algae and other soil microorganisms which require differing growth conditions or nutrients. Two or more PBRs may be also arranged in series in order to scale carefully controlled culturing steps according to the desired volume and optimal growth rates, typically by a capacity factor of 10 times. A PBR system of parallel and series PBRs increases the efficiency of the culturing process, enabling large scale production and distribution.

After growing in the PBR (or PBR system), the soil microorganisms are harvested and compounded using an integrated water extraction and compounding system. Admixes are positioned within a water extraction and drying process to compound additives that have the properties of being nutritional, preservative, are biologics, or that augment the drying mat of microorganisms for optimal dissemination, such as by adding density through the addition of clay. Biologics in this context can be single or multicellular organisms, or bio-active substances, including seeds, that enhance soil colonization by TerraDerm. The extraction system is composed of a porous filter belt that conveys the algae or soil microorganisms toward a dry end while extracting water via an underlying capillary belt. As water is removed, interstitial space makes room for the addition of admix compounds. The positioning of admixing and the rate of compounding are chosen to accommodate the wetness or dryness of the drying mat so that admix losses are minimized and binding is maximized. If the admix is combined to an overly wet portion of the extracted mat of microorganism, a greater portion of the admix will be extracted. Generally, a dry admix is positioned toward the end of the water-extracting portion of the conveying filter belt. After water extraction, but before final drying, a wet admix dispenser may be used to apply wet admix to the drying cake of algae and admix. Wet admix is positioned to ideally drive the dry admix into the moist mat or cake of soil microorganisms.

After admixing, a drying process ensures that the storage life of TerraDerm particles is adequate; generally a year or more is desirable. Coatings may be applied, after drying and shaping the particles, to create the TerraDerm product, which is spread upon farmlands or damaged land using standard agricultural practices, such as crop dusting, mixing with irrigation water or applying with spreading machines. Once on the soil surface, the natural availability of carbon dioxide and nitrogen in air, along with available participation or irrigation water and sunlight, causes the TerraDerm to induct a growing colony of soil microorganisms in proportion to the growth conditions for that specific consortium of microorganisms. The consortium of microorganisms in a locally adapted TerraDerm is preferably picked from local soil samples representing the best "Target Outcome" that could be expected from a soil crust reseeding effort of similar local soils. When this is done and the TerraDerm is spread to sufficient surface density, then the crust will reestablish at an accelerated rate well in advance of natural propagation. In land reclamation efforts, sufficient application density is approximately 0.1 to 2 TerraDerm particles placed per square cm. In agricultural applications where accelerated fertilization performance is required, sufficient application density is approximately 1 to 20 TerraDerm particles 26 per square cm.

Referring still to FIG. 1, as the TerraDerm microorganisms grow and propagate in and on the soil, their uptake of CO2 from the atmosphere increases proportionate with the population size, impinging sunlight, water availability, soil type and the occurrence of secondary vascular plant growth that might further increase the net primary productivity of the soil. The amount of CO2 drawn down from the atmosphere will vary widely dependent on these factors. It is estimated that if a crust is allowed to grow to maturity in a land reclamation application, that it will draw down from the atmosphere approximately 100 grams of CO2 per square meter per year. Advantageously, there exists a multiplier effect between the amount of CO2 used to manufacture TerraDerm and the amount of CO2 that will be drawn from the atmosphere yearly by its growth. The range in the forgoing estimation is on the order of 50x in a long-term land reclamation effort. For seasonal use on agricultural crops, the multiplier might be found to be as low as 1x, and yet this 1x yearly multiplier accumulates carbon in the soil and is of great interest to industry. The interest is because the CO2 can be channeled to TerraDerm production in one location while the application of that product in a second location can offset carbon emissions into the atmosphere stemming from anywhere on the planet since the atmospheric concentrations of CO2 homogeneously rebalance themselves through gaseous diffusion.

The various admixes optionally to be included are also desired to remain physically s associated with the microorganism consortium in the same relative proportions, even as the composite admix/biomass flake is reduced in size by granulation. By even layering and infusing of the admix homogeneously across the flake as the flake is being generated, then these relative proportions of admix/biomass can be maintained during the granulation and particle coating process. The dry admix components are further added as the biomass mat begins to consolidate, which helps to mechanically consolidate the dry admix with the biomass by entrapping some of the dry admix in the filaments of the consolidating cyanobacteria. The dry hopper dribbles dry admix onto Youngs' web belt between the first roller and the second roller as the belt begins to leave contact with the capillary belt of Youngs' apparatus. The amount of dry admix dribbled on the belt will be between 0.5 and 10x the dry equivalent mass of the microorganisms it is being dribbled on, The wet admix is typically, but not exclusively, a sugar based composition of xeri-protectants and heterotrophic consortium member nutrition additives that serve to bind and glue all the components together as it dries. Using an actual mucilage or other water soluble glue for this purpose, or a solvent based UV degradable binder, is to be considered as well for this purpose. The wet admix hopper is positioned to spray liquid admix onto the web belt after Youngs' web belt leaves contact with the capillary belt between the second roller and the third roller.

Admixes consist of nutritional elements, preservatives, biologics, and elements that prepare TerraDerm for dissemination. Biologics in this context can be single or multicellular organisms or bio-active substances, including seeds, that affect soil colonization by TerraDerm. The following are optional admixes acid their purpose:

1) Anti-oxidants such as beta carotene in a non-limiting case preserve the TerraDerm during the drying process and in storage.

2) Xeri-protectants such as sucrose and other sugars in a non-limiting ease prevent cell damage from rapid desiccation and extended desiccation overtime. At least one embodiment includes the use of a promising biologically derived xeri-protectant called trehalose.
3) Growth nutrients include micro nutrients needed by all soil microorganisms as taught by Flynn including sugars to feed the non-photosynthetic cohorts during the initial stages of establishment.
4) Sand or clay fillers serve two purposes. One is to increase the weight density of the resultant granulated particles thereby making them more aerodynamically spreadable from aircraft, and land based spreaders and resistant to wind currents. The other purpose is to provide a non-damaging location for fracture lines between the desiccated microorganisms during granulation that does not split through the microorganism itself.
5) Spread pattern tracers record dissemination patterns and may be fluorescent additives. Another tracing tag may be the use of inheritable but non-operational unique gene sequences within one of the microorganisms that will propagate at the same rate and with the same spatial characteristics as the TerraDerm propagates. This will allow a researcher or carbon credit auditor to visit a patch of soil months or years after initial application of TerraDerm and know how much of the soil crust or under-earth biomass is directly due to the propagation and beneficial actions of the specifically tagged TerraDerm.
6) Vascular plant seeds like restorative grasses or actual crop seeds may become part of admix. In this case the TerraDerm would be designed to work in biological concert with the embedded vascular plant seeds to achieve and maximize the desired restorative or fertilizing result.
7) Tackifier may be added to the admix in order to quickly bind the particle with other soil grains upon first environmental wetting to prevent further shifting by wind or water erosion. This assists in the dissemination of inoculant into the soil matrix.
8) Other microorganisms may be added to either the dry mix or to the wet mix. These other microorganisms may be chosen for their auxiliary properties like being a good tackifier or they may be chosen because they are an important part of the biological consortium of TerraDerm; yet for various reasons such as growth media type incompatibility or susceptibility to predation they were not able to be co-grown in the same photobioreactor as the rest of the TerraDerm consortium members.

Of course it should be recognized the above admix administration could be accomplished with other biomass extraction and drying equipment beyond Youngs' to include in a non-limiting fashion forms of spray drying including fluidized spray drying and fluidized granulation, refractive window belt drying and drum drying. Although not the current preferred embodiment, all of these methods allow that same homogeneous layering of admixes.

The purpose of this invention's processes in FIGS. 4 and 5 is to transport soil inoculant from the production PBR to the soil to be treated/fertilized in an effective and profitable manner. Essentially, the overall process to combine technologies, admixes and individual processes with the PBR output is achieved to yield a TerraDerm product that not only is effective in its application on soil, but that can be transported and stockpiled over time without degradation. Advantageously, techniques described herein facilitate manufacturing TerraDerm pellets that can be broadcast by a spinning spreader such that they are not blown away by the ambient wind. A further benefit includes that the TerraDerm is able to be distributed by agricultural aircraft. Yet a further embodiment is that the TerraDerm can be mixed with irrigation water and sprayed on crops. This adaptive ability is the function of the specifically selected inventive combination of processes depicted in FIGS. 4 and 5.

FIG. 5 concerns the conversion of homogenously layered biomass flakes into uniformly sized particles ideally having a high weight density and as spherically compact of a profile that is reasonably possible or commercially viable so as to maintain the fastest aerodynamic falling velocity which helps in the effectiveness of aircraft and spreader dispersal methods. Additionally, the more spherical profiles will be more predictable to optimize in the fluidized coating stage and will require less mass and cost of coating admixes to adequately cover them. Accordingly, the first process on FIG. 5 is passing the layered biomass flake through a flake crusher such as the Hosokawa model shown, or other equivalent methods, and crushed by rotors, providing uniformly sized particles. Screen size on the flake crusher is adjusted to create particle sizing. Ideally, the particle size produced by the flake crusher would be roughly equivalent to the layered flake thickness, thus forming the most compact physical profile. In this scheme, to adjust to a different particle size one would first adjust the flake thickness produced by the belt harvesting and drying apparatus by slowing the belt to create a thicker flake and faster to produce a thinner one. Then the screen size on the flake crusher would be adjusted to create particle sizing that is the same or slightly larger than the flake thickness by an approximate ratio of 1.0 to 1.7. The resultant particles in the size range depending on the field and spreader application details would be approximately 0.5 to 1.5 mm diameter. These particles are then entrained in a blower feed into the fluidized bed particle Coater. Particle coater suspends granulated flakes within an updraft of air created by blower-while coating is injected through coating spray nozzles. A cyclone or other particle size winnower can remove the dust before being passed to the coater.

There are many kinds of batch and continuous coater technologies that would be suitable for applying the optional coating admixes to the outside of the particle. The preferred method is a continuous coating process, of which the shown Hunttlin coater is an example. Coating substances may be selected to provide the following functions: anti-caking, anti-friction, delayed-release, spread pattern tracers, tackiflers, biologics and others in this non-inclusive list.

The prospective purpose of these listed coatings is recounted below:

1) Anti-caking coatings like clay or talc or others may be applied as a last step in a serial coating process and serve to prevent the TerraDerm particles from sticking or clumping together during any part of their transportation, storage or use cycle.
2) Anti friction coating that also may include talc or thin polymer coatings may be applied as the outermost layer to enhance the spreading efficiency when used with mechanical spinning disk spreaders whose eject velocity is retarded by surface friction during the blade slinging phase of dispersion.
3) Delayed release coating may be compounded from water soluble gels or from thin layers of UV degradable solvent based polymer. In both cases, the purpose is to be able to mix the TerraDerm particles along with a water carrier for enough time that the water can be used as the distribution media, such as from a crop duster aircraft or irrigation sprayer system, without activating or damaging the viability of the particle's entrained microorganisms via premature wetting and release. Of course, in some cases allowing the TerraDerm particles to completely dissolve in a liquid distribution carrier may not hurt the viability of the organisms at all, particularly if they are distributed with a minimum of elapsed hydration time and ensuing metabolic activity prior to being distributed onto the ground and minimum occurrence of high hydrodynamic shear from pumps and nozzles.

4) Spread pattern tracers are the addition of fluorescing dyes into the coating such that after an application of TerraDerm on a patch of soil has occurred, then the efficacy of the application means can be assessed by illuminating the surface with UV light and photographing the particle spread density using a fluorescence wavelength transmitting lens filter to highlight the particles.

5) Water soluble tackifiers may be added to the outer layer such that after the particle lands on the soil surface and encounters moisture that it glues itself to adjoining soil grains, thus inhibiting its shifting or loss through wind and ensuing water erosion. The tackifiers may be of substances such as guar gum or sugars or algal based polysaccharides or cells bathed in polysaccharides that may be bred for this purpose as biological tackifier cohorts in the PBR or grown separately in their own bioreactor and added as dry or wet admixes.

6) Biologics may also be spray coated onto the exterior of the particle. In this context "biologics" can refer to whole living or dead cells or bio-active substances that affect the receptivity of the soil to being colonized by the TerraDerm microorganisms. Alternatively, these substances may be intended to prevent the consumption or destruction of the TerraDerm by other living organisms such as insects, other microorganisms, birds or other living creatures.

In one embodiment, a large scale PBR or array of PBRs is employed in a commercial scale-up of TerraDerm production. A PBR will not consume CO2 at night, and in fact, will produce a little CO2 at night itself as the microorganisms oxidize their internal food reserves to provide operational energy. Additionally, during inclement weather when the sun does not shine, the PBRs will not consume CO2 either. Accordingly, a system of PBRs needs to have a buffer storage system for CO2 if it is to rate match with a constant delivery stream typically envisioned to be provided by industry. In this scheme, the PBR would draw down on its own stored CO2 reserves when the sun is shining strongly and the reserves would accumulate at night or when the weather is inclement. Nominally, it is conceived that a 1 week (approximately 1 ton per half acre of PBR area) CO2 buffer reserve will be sufficient to damp out most diurnal and weather related uptake variations. At standard temperature and pressure, 1 ton of CO2 has a density of approximately 2 grams/liter and will occupy a volume of 500,000 liters or 500 cubic meters. For frame of reference, a gas exchange housing associated with a PBR of half acre size is conceived to be 15 meters wide and 10 meters long. If this 1 week supply of CO2 were contained in an inflatable bladder covering the gas exchange end housing area, then the bladder would stand on average about 3.3 meters high when full. Accordingly it is conceivable that each half acre of PBR area can be associated with inflatable structures that double as gas storage enclosures. However, one would not want the rain or snow shedding capabilities of such a structure to degrade as they are deflated, so the use of a permanently inflated structure with an inner gas separation barrier is far more practical from an architectural standpoint.

FIG. 6 shows how a CO2 storage buffer system might work. In this figure, an algal farm (perhaps producing TerraDerm) containing 100's or thousand's of PBRs according to the above description would be nominally fed by.a high pressure CO2 pipeline that would often be part of a distribution grid having many CO2 sources, such as power plants, cement plants, and coal-to-liquid plants to name a few. Also, there would be on this network many CO2 sinks, such as algae farms, underground sequestration storage or enhanced oil recovery operations.

There are two kinds of CO2 storage shown in FIG. 6 and they do not need to be used together, but are used together in the preferred embodiment. In this concept, algae farm locations are partially selected by virtue of having leasable or own-able carbon capture and sequestration (CCS) "pore-space" in the geologic strata beneath them. There is a legal/regulatory and technical synergy available to operators of both operations by locating an algal farm over a CCS repository. While we as a country have not yet fully settled on the legal regulatory requirements for CCS, strict monitoring of the landscapes over the sequestration sites to detect potential leaks will be important. One way to achieve this is to own the land over the CCS sites, and by having an algal farm built over the sites the farm will have a vast buffer of CO2 reserves during the years it may require to fully fund and build out a fully scaled algal facility. Nominal calculations of the underground CO2 plume size in a CCS project show that for a given tract of land the CCS storage capacity would be about 30 times the yearly uptake of CO2 by an algal farm laid over an equivalent stretch of land on the surface. Accordingly, certain financial and regulatory synergies could be enabled by beginning an underground CCS project on a site in the near-term, while committing to build a similar scale algal farm on top of the reserve site over the ensuing decades, In this way, the CO2 uptake capacity of a specific CCS/Algal farm site would never saturate and could evolve into a long-term source of products (TerraDerm being one of many potential algal based products) manufactured photosynthetically by algae from the CO2.

Accordingly, in FIG. 6 the CO2 is input into the system and may be compressed further to enable geologic storage. Since the algal farm needs only enough pressure to distribute CO2 around the farm, then the pipeline pressures could be reduced for farm use through an expansion turbine and the energy recovered as electricity net metered onto the power grid. The low pressure gas would be stored in low pressure inflatable structure that either stand alone or are part of each PBR. In these structures would be a loose separation diaphragm. On one side, a pressure controlled system consisting of a compressor and a pressure sensor inflates the structure to a nominal pressure as required to resist local wind and snow load and comply with local building regulations. On the other side of the diaphragm, CO2 could be pumped into the dual-chamber inflated structure at a constant pressure since the air pressurized side would release air to maintain the overall structure's pressure. Through this scheme, an algal farm can be sized to handle the average yearly influx of CO2 from industry without worrying about stretches of bad weather or even winter-summer sun exposure variability.

In an additional and important embodiment, a similar storage system could be built to accommodate the oxygen produced by algal farms and subsequently to deliver that oxygen to industry or on-site used through pipeline systems similar to the CO2 pipeline systems described above. The oxygen storage can be located in independent inflated structures, or can share the same structure as the CO2 storage by simply employing a second loose diaphragm separated partition within the same overall pressurized structure that the CO2 storage uses.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

All values, dimensions and ranges as provided herein and in the associated figures are exemplary and given for purposes of enablement and are not to be considered limiting unless claimed; accordingly, other values, dimensions and ranges are within the scope of the invention.

Various embodiments of the present inventions are set forth in the attached figures and in the Detailed Description as provided herein and as embodied by the claims. It should be understood, however, that this Summary does not contain all of the aspects and embodiments of the one or more present inventions, is not meant to be limiting or restrictive in any manner, and that the invention(s) as disclosed herein islare understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

To further clarify the above and other advantages and features of the present invention, a more particular description of the invention is rendered by reference to specific embodiments thereof which are illustrated in the appended drawings. It is appreciated that these drawings depict only typical embodiments of the invention and are therefore not to be is considered limiting of its scope. The invention is described and explained with additional specificity and detail through the use of the accompanying drawings in which.

DETAILED DESCRIPTION OF THE PREFERRED EMBODIMENT

Figure 1:
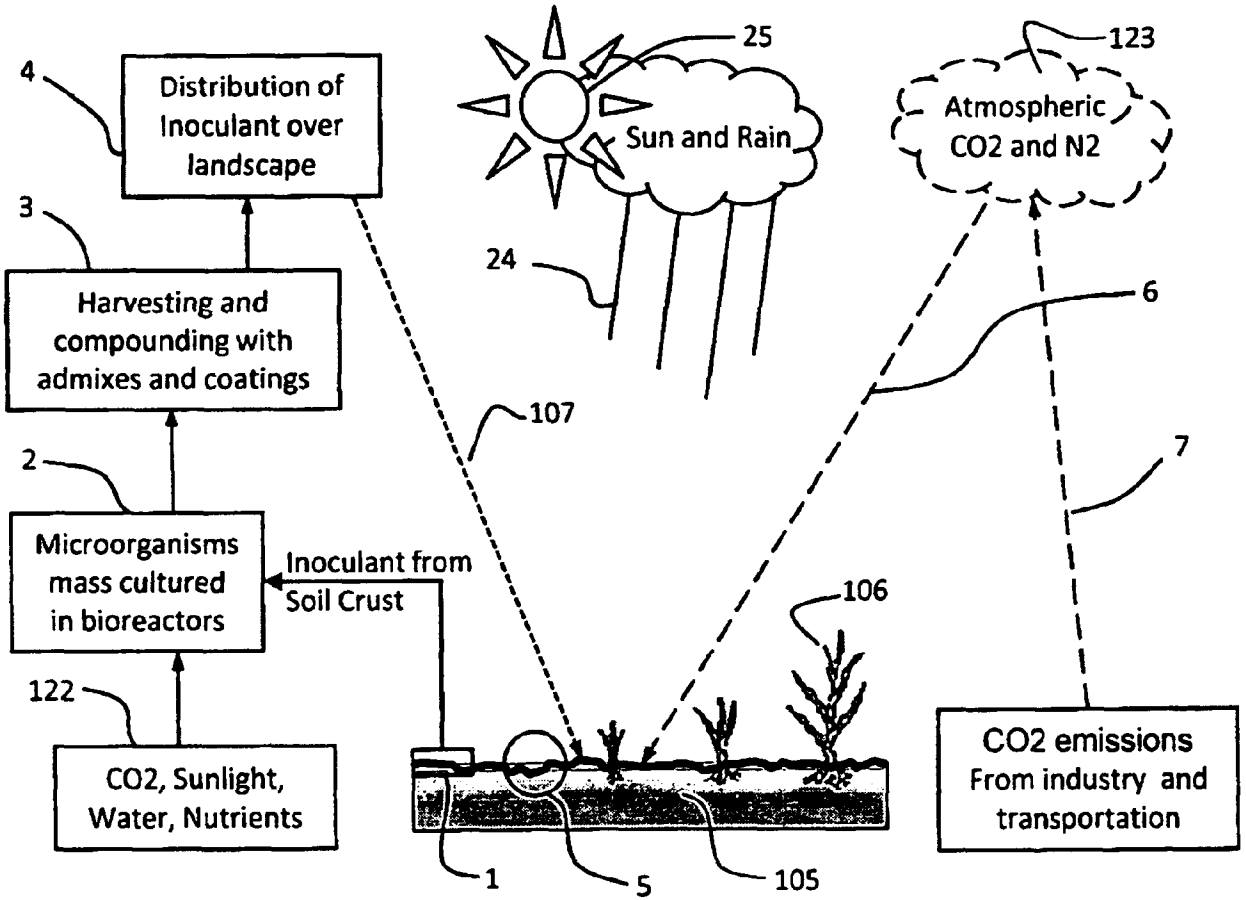
FIG. 1 describes the field of the invention.

Referring to FIG. 1, a biological culture of natural soil microorganisms 1 is drawn from their normal residence in the top centimeter of healthy undisturbed soil 105 found in un-shaded areas. These blue-green algae and their soil consortia 1 are cultured into an inoculant and used to inoculate an amplifying Photobioreactor 2, where the culture can be rapidly grown in liquid media via ready access to nutrients, carbon dioxide and sunlight 122. The photobioreactor 2 can be effected through a number of designs differing in levels of performance and features; however the preferred designs are biologically closed so that the soil crust microorganisms 1 can be grown in an environment protected from invasion by competing algal species that may be better adapted for propagating in the aqueous environment. The PBR 2 is fed by sunlight 25, nutrients and a carbon source 122 that is most commonly carbon dioxide, but that may be a fixed form such as sodium bicarbonate or other bio-available forms. After growing in the PBR 2, the soil microorganisms 1 are harvested and compounded using admixes and coatings 3 to create the product TerraDerm 107 that can be spread upon farmlands or damaged land using standard agricultural practices, such as crop dusting, mixing with irrigation water or applying with spreading machines 4. Once on the soil surface, the natural availability of carbon dioxide and nitrogen in air 123, along with available participation or irrigation water 24 and sunlight 25, causes the TerraDerm 107 to induct a growing colony 5 of soil microorganisms in proportion with the suitability of growth conditions for that specific consortium of microorganisms. Referring still to FIG. 1, as the TerraDerm microorganisms 5 grow and propagate in and on the soil, their uptake of CO2 6 from the atmosphere increases proportionate with the population size, impinging sunlight, water availability, soil type and the occurrence of secondary vascular plant 106 growth that might further increase the net primary productivity of the soil 105. The amount of CO2 6 drawn down from the atmosphere 123 will vary widely dependent on these factors.

Figure 2:
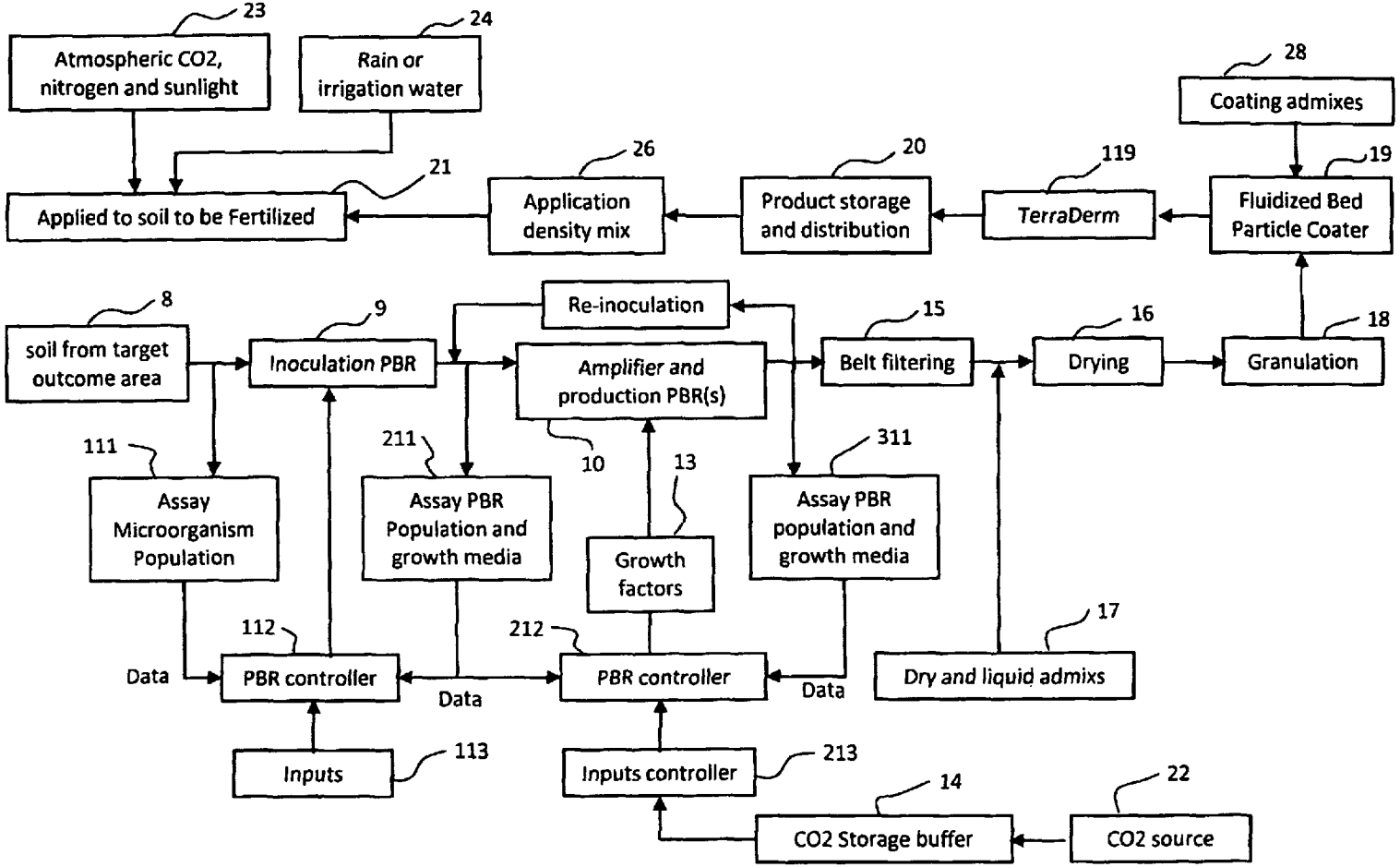
FIG. 2 is a block diagram of the production process.

Referring to FIG. 2, a sample of the top cm of soil 8 is used to inoculate a small PBR 9 that itself can create a larger volume of inoculant for a larger PBR 10. In at least one embodiment of the one or more present inventions, the soil sample is drawn from a desired "Target Outcome" soil patch 8 that represents the best and most desired microbiological outcome for the treated soil, and that is similar in non-biological constitution and environmental factors to the soil in the area to be treated. In this way, a consortium of microorganisms can be specifically selected to manufacture a particular regional type of TerraDerm that includes microorganisms most favored to survive, thrive and fertilize on the targeted soil to be treated in that region.

In FIG. 2. an inoculation PBR 9 is followed by one or more amplifier PBRs 10, and maybe followed by one or more production PBRs 10. Amplifier and production PBRs 10 may be in series and/or parallel arrangement in which separate cultures are grown and/or concatenated, finally combined to feed belt filtering system 15. Inoculation PBR 9 releases the organisms from the Target Outcome soil 8 and begins growing a population facsimile within the PBR's liquid medium. The population generated by the inoculation PBR 9 should have substantially the same or otherwise sufficient microorganism consortia members and in roughly substantially the same or otherwise sufficient balance as they were present natively in the soil. The inoculation PBR operator uses input and output population and growth media assay data 111 to adjust controller 112, which regulates inputs 113 such as light, pH, temperature, CO2 and nutrient levels, as well as mixing speed, to effect the desired growth rate and population balance characteristics on the output of the incubator. In a similar fashion, the amplifier and production PBR operator looks at the population and growth media assay 211 and 311 between the input and output of the PBRs and adjusts controller 212, which regulates inputs 213 to effect the desired result. PBRs typically need to be inoculated by the fully populated media from a PBR 1/10 their size, and so amplifier PBRs are often designed in decade-size steps to finally create the inoculant quantity needed for the production PBR. At any step in the amplification or production PBR chain, the system can be used to continuously re-inoculate itself by simply not harvesting all the microorganisms, but leaving a sufficient "starter batch" behind. In all these processes, preferably the operator adjusts the growing conditions (or causes them to be adjusted) to maintain the desired growth rate and population ratio needed for the final product. In some cases, the desired product population ratio may be different from that found in the Target Outcome soil, but will affect a better result upon application via that difference.

In FIG. 2, the controller 213 for the production PBRs 10 show that the CO2 22 may be provided by a storage buffer 14, if needed, to match the rates of industrial CO2 22 delivery to the uptake rate of the PBRs 10, which is governed by the amount of daily and seasonal impingent sunlight and other environmental and operational factors such as temperature and mixing speed 13. At least one embodiment of this storage buffer is described and shown in FIG. 6.

Figure 4:
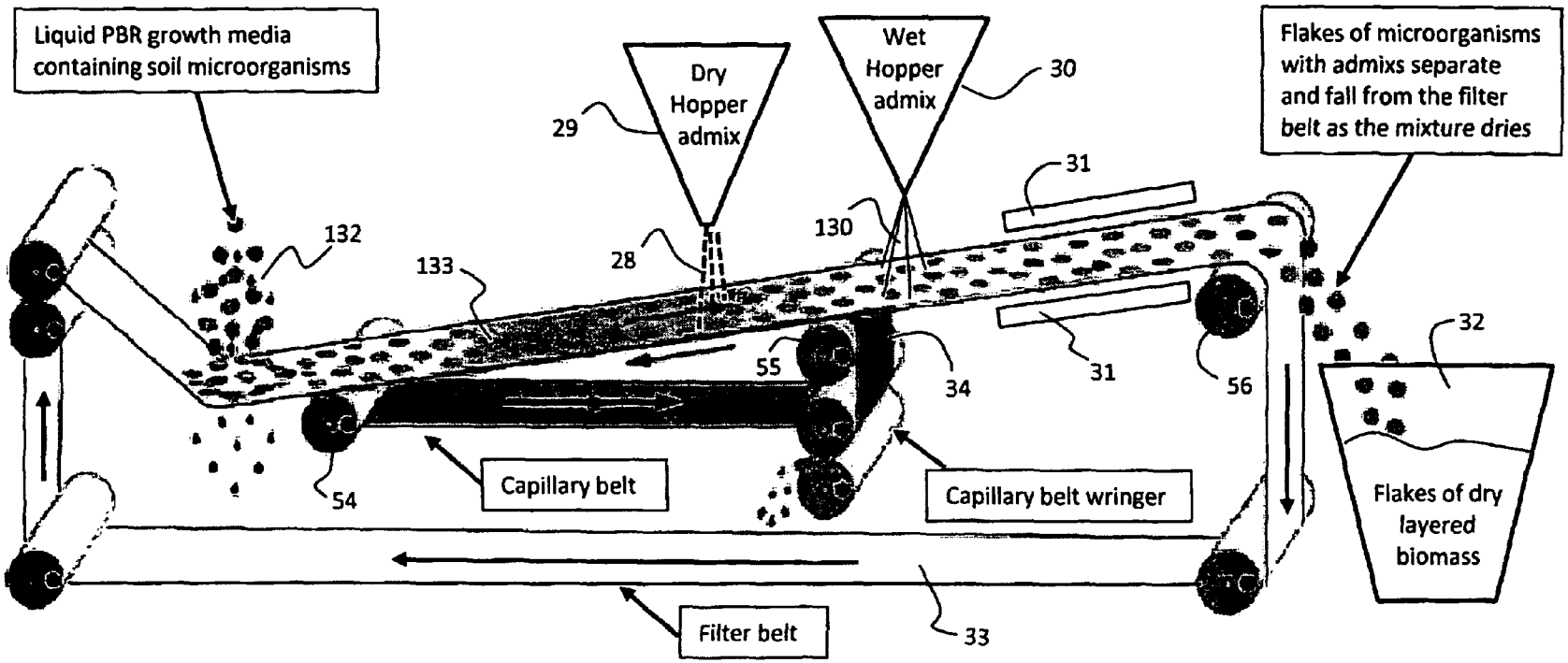
FIG. 4 is a diagram of belt extraction, compounding, and drying.

Referring again to FIG. 2, the output of the production PBR 10 is fed into the belt filtering 15 and belt drying 16 blocks in which various optional admixes 17 are combined in a process described in FIG. 4. Further, the granulation of the resultant dry flake 18 and its optional coating 19 to become TerraDerm is described on Figures. Still further, in FIG. 2 the final TerraDerm product 119 can be seen moving through distribution step 20 and being applied to soil 21 via various agricultural and land restoration spreaders, where atmospheric CO2 and sunlight 23 combine with rain or irrigation water 24 to revive TerraDerm particles 119.

Figure 3:
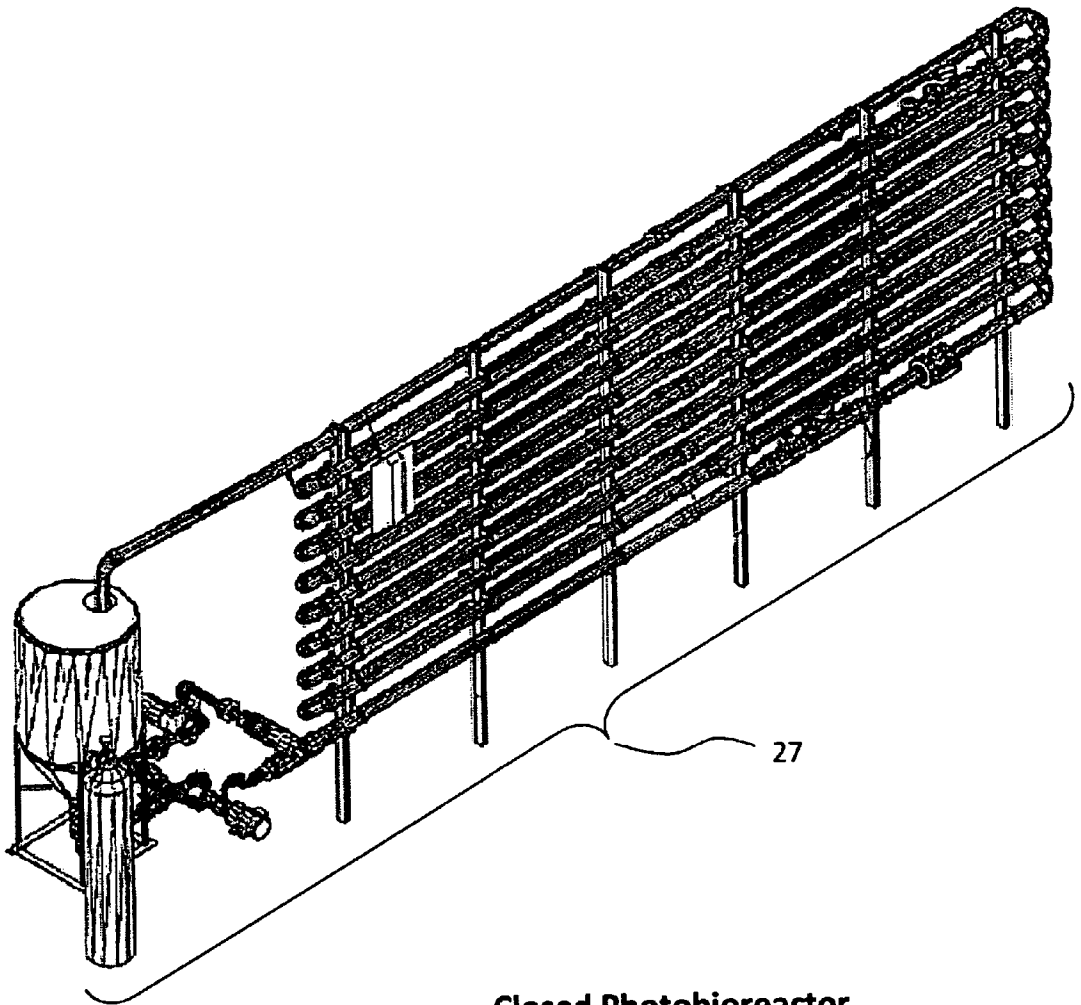
FIG. 3 is a low-volume closed photobioreactor and harvester.

Referring to FIG. 3, a low-volume pilot scale PBR 27 is shown with extractor and harvester, copied from Flynn.

Figure 5:
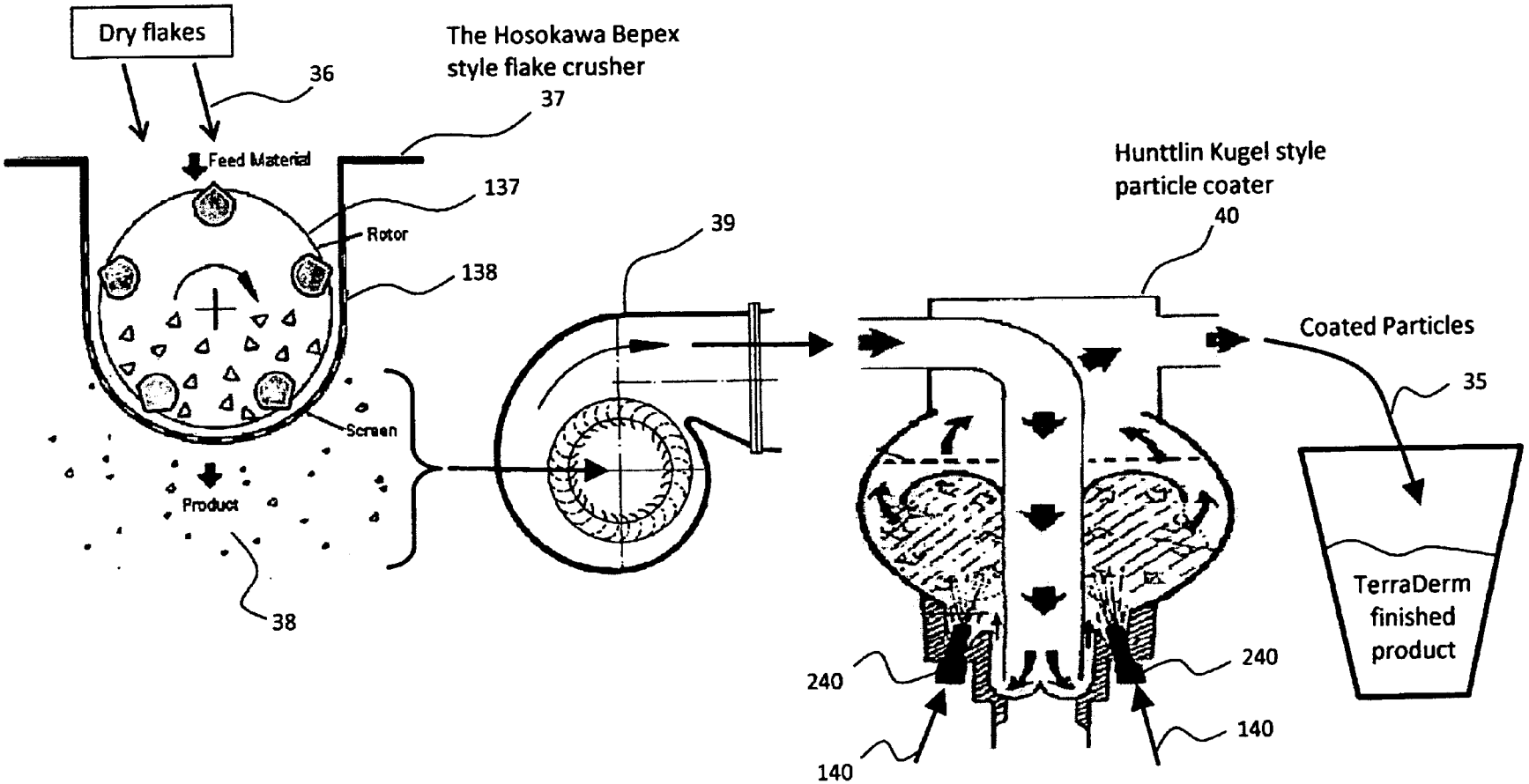
FIG. 5 is a diagram of flake granulation and coating.

Referring to FIG. 4 liquid growth media 132 is pumped onto conveying filter belt 33 where it is consolidated into a spongy mat of biomass 133. As biomass 133 moves up the conveying belt 33, capillary belt 34 moves underneath belt 33 and in the opposite direction, wicking water through belt 33 and extracting water from biomass 133. Solids content of biomass 133 increases from a starting point of about 10% at roller 54 and increasing until the texture of the biomass becomes moist and cakelike, with a solids content of about 14% to about 28% near second roller 55. Dry hopper 29 dispenses dry admix 28 onto biomass 133 at a location just before roller 55. Water is drawn from the mat of biomass 133, consolidating dry admix 28, which can be composed of various nutrients, preservatives, and/or dissemination agents. Following second roller 55, wet admix 130 may be dispensed from wet hopper 30 onto the biomass 133, compounding dry admix 28 into the biomass 133. Dryers 31 remove remaining water to produce flakes 32, which break away as belt 33 bends around roller 56. Flakes 32 of dry compounded, layered biomass are collected for feeding to the granulation process (FIG. 5).

In this context, "intimate" means that admixes are layered upon, and infused into, the web of algae 33. Each flake portion represents the same population ratios as is found in the PBR culture. An advantage of using Youngs' technology is that the dewatering process is gentle and effective, leaving another approximately 30% by weight in water to be removed later on the belt's path by low temperature evaporation.

In Youngs, experiments show that the solids content is typically about 10% at the beginning—the wet end—of the dewatering process, and in the range of 18-25% at the end of the dewatering process. The texture of the biomass after dewatering is moist, and is described as a cake. Moisture content will vary substantially with differing varieties of algae and other types of dewatered biomass, as it will with the speed of the conveying filter belt. Assuming an additional 7% (=25%-18%) of variability will occur with other untested biomass types and with varying belt speed, one might expect the solids content reported in Youngs' experiments to broaden to a 14-28% range at the end of the dewatering process in the wide range of applications anticipated for the invention being described.

The use of gentle and low temperature drying processes serves to preserve the growth viability of the TerraDerm microorganisms. Generally, it is preferred that drying temperatures remain below 140 degrees Fahrenheit to preserve the capacity of TerraDerm to revive in the presence of sunlight and water because 140 degrees is a maximum BSC temperature occurring on hot sunlit land where microorganisms remain viable. However, other kinds of drying, whether radiant, convective, or extractive, may have maximum temperatures that differ from 140 degrees Fahrenheit depending on whether the temperature is measured at the surface of the microorganisms, in the air, or at a source of heat. Additionally, slower or faster drying times will likely have different maximum temperatures that still preserve the viability of dried TerraDerm particles.

Referring to FIG. 5, flakes 36 enter flake crusher 37 where rotors 137 reduce flakes 36 into uniform particles 38 exiting screens 138, with particle diameter ranging from about 0.5 mm to 1.5 mm. Flakes 38 are sucked into blower 39 and projected into coater mechanism 40, where coatings 140 are injected through coating spray nozzles 240 to create coated particles 35.

Coating substances, as mentioned earlier, may be selected to provide the following functions: anti-caking, anti-friction, delayed-release, spread pattern tracers, tackifiers, biologics and others in this non-inclusive list.

Figure 6:
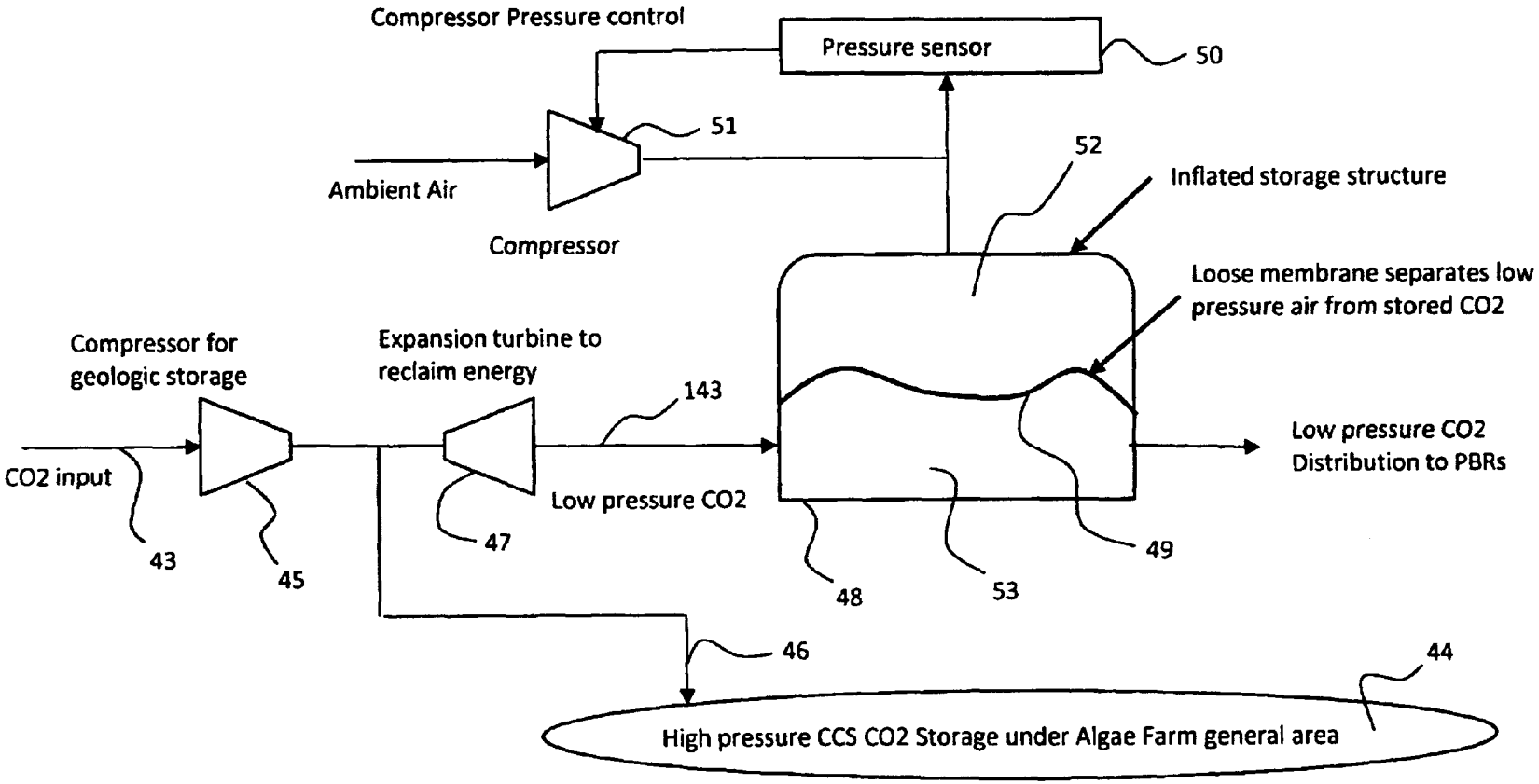
FIG. 6 is a diagram of CO2 distribution, bladder storage, and under farm storage.

Referring to FIG. 6, CO2 input pipeline 43 from any source of concentrated CO2 feeds CO2 into compressor 45 which may be directed to geologic storage line 46 and into underground pore space 44. CO2 43 may also be directed into inflatable storage structure 48 through expansion turbine 47. Excess CO2 in pore space 44 may be routed to inflatable structure 48 for low pressure circulation around the algal farm. Separation diaphragm 49 contains CO2 53 below it and plain air 52 above it at sufficient pressure to support snow and rain, should it be an external structure. Ambient air compressor 51 and sensor 50 maintain sufficient pressure and allow the CO2 storage volume 53 to vary without changes to storage pressure. On one side, a pressure controlled system consisting of a compressor 51 and a pressure sensor 50 inflates the structure to a nominal pressure as required to resist local wind and snow load and comply with local building regulations. On the other side of the diaphragm 53, CO2 143 could be pumped into the dual-chamber inflated structure at a constant pressure since the air pressurized side would release air to maintain the overall structure's pressure. Through this scheme, an algal farm can be sized to handle the average yearly influx of CO2 from industry without worrying about stretches of bad weather or the changes in algal farm CO2 uptake that will occur due to winter-summer and daily sun exposure variability.

In an additional and important embodiment, a similar storage system would be built to accommodate the oxygen produced by algal farms and subsequently to deliver that oxygen to industry or on-site used through pipeline systems similar to the CO2 pipeline systems described above. The oxygen storage can be located in independent inflated structures, or can share the same structure as the CO2 storage by simply employing a second loose diaphragm separated partition within the same overall pressurized structure that the CO2 storage uses.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The one or more present inventions, in various embodiments, include components, methods, processes, systems and/or apparatus substantially as depicted and described herein, including various embodiments, subcombinations, and subsets thereof. Those of skill in the art will understand how to make and use the present invention after understanding the present disclosure.

The present invention, in various embodiments, includes providing devices and processes in the absence of items not depicted and/or described herein or in various embodiments hereof, including in the absence of such items as may have been used in previous devices or processes (e.g., for improving performance; achieving ease and/or reducing cost of implementation).

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention (e.g., as may be within the skill and knowledge of those in the art, after understanding the present disclosure). It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for culturing and compounding a symbiotic consortium of cyanobacterial algae and other soil microorganisms into a stable, dry soil crust inoculant suitable for broadcast or crop duster spreading over land targeted for recovery, fertilization or mitigating the build-up of atmospheric carbon dioxide, comprising:

a culturing means for massing said consortium of soil microorganisms within an aqueous medium;

a porous extracting belt receiving said aqueous medium from above a wet end and conveying said consortium of soil microorganisms to a dry end and extracting water to underneath said belt, leaving a moist mat of soil microorganisms, said moist mat being further conveyed to a drying means;

a dispensing means dispensing admix onto said moist mat of soil microorganisms at a location between the midpoint of said extracting belt and said drying means, leaving a compounded mat, said admix having at least one of the following properties: nutritional, preservative, biologics, and dissemination;

a drying means drying said compounded mat sufficiently dry in order that the resulting flakes of inoculant are stable in storage for at least one year; and a reducing means reducing said flakes to roughly spherical inoculant particles suitable for broadcast or crop duster spreading over land.

2. A system as in claim 1, further including coupling industrial emissions of CO2 to said culturing means through a dynamic storage buffer having a variable containing volume at substantially constant pressure, wherein the CO2 demand of said culturing means varies by at least a factor of two over a 24 hour period.

3. A system as in claim 2, wherein said dynamic storage buffer is a subterranean pore-space beneath said culturing means.

4. A system as in claim 2, wherein said dynamic storage buffer is a inflatable storage system on the same grounds as the culturing means, said inflatable storage system having a separation diaphragm for maintaining substantially constant pressure as said storage volume varies.

5. A system as in claim 1, wherein said culturing means is a photobioreactor.

6. A system as in claim 5, wherein an amplifier photobioreactor is followed by a production photobioreactor having about 10 times the capacity as said amplifier photobioreactor for efficiently scaling the production of said consortium of microorganisms.

7. A system as in claim 1, wherein said soil microorganisms consists of at least one of the following: algae, fungi, lichens, and bacteria to enhance soil crust inoculation.

8. A system as in claim 1, further including a capillary belt wicking moisture from underneath said porous extracting belt and moving in the opposite direction.

9. A system as in claim 1, wherein said dispensing means is composed of a dry dispensing means dispensing dry said admix at a location near the end of said extraction belt and chosen to avoid admix loss due to said extraction, and followed by a wet dispensing means dispensing wet said admix at a location optimized to drive said dry admix into the interstitial space within said moist mat created by said extraction.

10. A system as in claim 9, wherein said dry dispensing means is a hopper.

11. A system as in claim 9, wherein said wet dispensing means is a sprayer.

12. A system as in claim 1, wherein said drying means is a blower blowing low temperature air in order that said flakes of inoculant are revivable.

13. A system as in claim 1, wherein said drying means is evaporative drying in ambient air.

14. A system as in claim 1, wherein said reducing means is a flake crusher.

15. A system as in claim 1, further including a coating means positioned after said reducing means for coating said flakes with fluids having at least one of the following properties: anti-caking, anti-friction, delayed release, tracers, biologics, and tackifiers.

16. A system as in claim 1, wherein inoculant particles are broadcast by a crop dusting airplane.

17. A method of culturing and compounding a symbiotic consortium of cyanobacterial algae and other soil microorganisms into a stable, dry soil crust inoculant suitable for broadcast or crop duster spreading over land targeted for recovery, fertilization or mitigating the build-up of atmospheric carbon dioxide, comprising:

culturing a consortium of soil microorganisms within an aqueous medium; extracting said soil microorganisms from said aqueous medium, leaving a moist mat of soil microorganisms;

layering admix onto said moist mat leaving a compounded mat, said admix having at least one of the following properties: nutritional, preservative, biologics, and dissemination;

drying said compounded mat so that resulting flakes of soil inoculant are stable in storage for at least one year; and reducing said flakes to roughly spherical, spreadable inoculant particles.

18. A method as in claim 17, further including coupling industrial CO2 to said culturing means.

19. A method as in claim 17, further including broadcasting said inoculant particles by a crop duster aircraft.

* * * * *